United States Patent [19]

Musser et al.

[11] Patent Number: 4,563,463
[45] Date of Patent: Jan. 7, 1986

[54] 2-OXO-1,3-OXAZOLO[4,5-H] QUINOLINES USEFUL AS ANTI-ALLERGY AGENTS

[75] Inventors: John H. Musser, Malvern, Pa.; Richard E. Brown, East Hanover, N.J.

[73] Assignee: USV Pharmaceutical Corp., Tarrytown, N.Y.

[21] Appl. No.: 667,667

[22] Filed: Nov. 2, 1984

Related U.S. Application Data

[63] Continuation-in-part of Ser. No. 476,673, Mar. 18, 1983, Pat. No. 4,522,947, which is a continuation-in-part of Ser. No. 362,712, Mar. 29, 1982, abandoned.

[51] Int. Cl.[4] .................. C07D 498/04; A61K 31/47
[52] U.S. Cl. ...................................... 514/293; 546/83
[58] Field of Search ........................... 546/83; 514/293

[56] References Cited

U.S. PATENT DOCUMENTS 4,474,786 10/1984 Smith et al. .......................... 546/83

Primary Examiner—Henry R. Jiles
Assistant Examiner—Dale A. Bjorkman

[57] ABSTRACT

New quinoline compound, and the corresponding 1,2-; 1,3-; and 1,4-benzodiazines, the quinoline compounds being of the formulae:

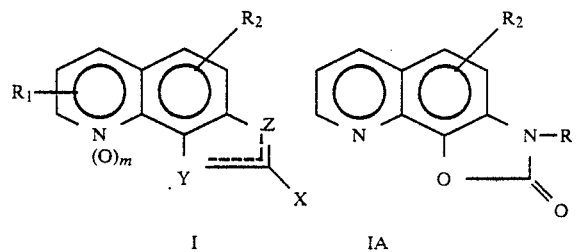

and salts thereof, wherein

R is hydrogen, acyl, carboethoxy,(3-methoxyphen-)acetyl,(2-phenyl)propionyl, dimethylcarbamoyl or methyl, $R_1$ and $R_2$ are independently hydrogen, lower alkyl, halo, trifluoromethyl, amino, lower alkyl amino, lower acylamino, cyano, aryl, aryl/lower alkylene, nitro, lower alkynyl, lower alkenyl, lower alkyl sulfinyl, lower alkyl sulfonyl, lower alkoxycarbonyl, carboxyl, lower alkoxy, lower alkanoyl, or lower alkenoyl, Y is oxygen, sulfur, nitrogen or $R_3N$ wherein $R_3$ is hydrogen, lower alkyl, alkenyl, alkynyl, aryl, aralkyl, acyl, aminoalkyl, or carboxyalkyl, Z is oxygen, sulfur or nitrogen, X is cyano, carbalkoxy, carboxyl, formyloximino, tetrazolyl, carbalkoxyalkyl or carboxyalkyl, and m is 0 or 1, are useful as medicinals, especially for treatment of asthma, and/or as intermediates in the preparation of compounds useful for treating asthma.

3 Claims, No Drawings

2-OXO-1,3-OXAZOLO[4,5-H] QUINOLINES USEFUL AS ANTI-ALLERGY AGENTS

This application is a continuation-in-part of now pending U.S. application Ser. No. 476,673 filed Mar. 18, 1983 now U.S. Pat. No. 4,522,947, which application in turn is a continuation-in-part of U.S. application Ser. No. 362,712, filed Mar. 29, 1982, now abandoned.

This invention relates to new quinoline compounds and the corresponding 1,2-; 1,3-; and, 1,4-benzodiazines, the new quinolines being of the general formulae:

and salts thereof, wherein

R is hydrogen, acyl, carboethoxy, methyl, (3-methoxyphen)acetyl, (2-phenyl)propionyl or dimethylcarbamoyl, $R_1$ and $R_2$ are independently hydrogen, lower alkyl, halo, trifluoromethyl, amino, lower alkyl amino, lower acylamino, cyano, aryl, aryl/lower alkylene, nitro, lower alkynyl, lower alkenyl, lower alkyl sulfinyl, lower alkyl sulfonyl, lower alkoxycarbonyl, carboxyl, lower alkoxy, lower alkanoyl, or lower alkenoyl, Y is oxygen, sulfur, nitrogen or $R_3N$ wherein $R_3$ is hydrogen, lower alkyl, alkenyl, alkynyl, aryl, aralkyl, acyl, aminoalkyl, or carboxyalkyl, Z is oxygen, sulfur or nitrogen, X is oxygen, cyano, carbalkoxyl, carboxyl, formyloximino, tetrazolyl, carbalkoxyalkyl or carboxyalkyl, and m is 0 or 1.

The invention, in its broad aspects, includes derivatives of quinoline, and corresponding benzodiazine compounds of formula I. Within this broad group, because of their properties, certain subgroups are preferred over others. These compounds have utility as medicinals, especially for treatment of asthma, and/or as intermediates in the preparation of compounds useful as medicinals.

In the preferred compounds, Z is nitrogen, $R_3$ is hydrogen, alkyl aminoalkyl or carboxyalkyl of from about 1-5 carbon atoms and m is 0.

It is preferable that when Y is oxygen, that Z be nitrogen; that when Z is sulfur, that Y be nitrogen; and that when Z is nitrogen, that Y be oxygen, sulfur or $R_3N$.

In the most preferred compounds, Z is nitrogen and Y is oxygen. In slightly less preferred compounds, Z is oxygen and Y is nitrogen.

When X includes an alkyl group, it is preferred that the alkyl contain 1 to 5 carbon atoms.

The preferred X groups are those including carboxy groups and, more preferably, carboxy groups directly attached to the ring. These groups include those having the general formula $$(CH_2)_a-\overset{O}{\underset{\|}{C}}-OR_4$$

wherein a is 0 or 1, preferably 0, and $R_4$ is H or a lower alkyl group, preferably having 1–12 carbon atoms, more preferably having 1–5 carbon atoms, or an alkyl group substituted with an alkoxy or amino group. $R_4$ can also be a metal or organic cation, preferably an alkali metal cation.

The compounds in which X is formyloximino or cyano are preferred as intermediates in a process for making the preferred carboxy compounds of this invention.

More than one $R_1$ or $R_2$ substituent can be on the respective rings. It is preferred that $R_1$ be hydrogen, $C_1$–$C_5$ alkyl, particularly methyl or ethyl, halo, particularly chlorine or bromine, trifluoromethyl or benzyl. It is most preferred that $R_1$ is hydrogen. It is preferred that $R_2$ be hydrogen, $C_1$–$C_5$ alkyl, halo, particularly chloro, trifluoromethyl, nitro, $C_1$–$C_5$ alkylamino or acylamino. It is most preferred that $R_2$ be at the 5 position.

The preferred compounds include those in which the quinoline ring structure is present. As is already indicated herein, the present invention also embraces the corresponding benzodiazines, e.g., 1,4-benzodiazines of the formula:

as well as the 1,2- and 1,3-benzodiazines. The invention is illustrated by way of the preferred quinoline compounds but it is within the skill of the art to extend the illustrations to benzodiazines.

The quinoline compounds of the present invention can be prepared, in general, by reaction of the following compounds under condensation conditions to form the desired heterocyclic ring:

wherein
$R_1$, X, Y, Z and $R_2$ are as herinbefore defined;
n=1 except when Y or Z is N when n=2; and
R=a di- or trifunctional group capable of condensing with $Y(H)_n$ and $Z(H)_n$ to form the indicated heterocyclic ring, e.g., trihalomethyl, trialkoxymethyl, or formyloximino.

A typical procedure for preparing the present new quinoline compounds where Z is N and Y is O, S or $R_3N$ follows:

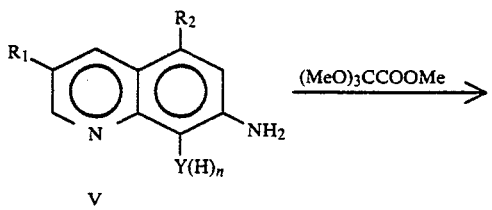

V

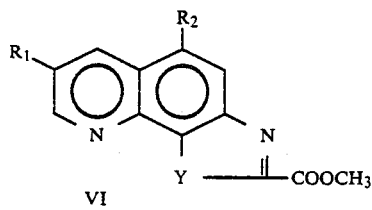

VI

In this illustration, X is carbomethoxy but may be any of the groups representative of X.

A particularly preferred procedure for production of the present new compounds, especially the preferred compounds in which X is a carboxy group attached to the ring involves condensation of

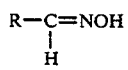

with a selected 7-amino-8-hydroxyquinoline to form the corresponding 2-formyloximino-1,3-oxazolo[4,5-h]quinoline from which the corresponding cyano compound can be prepared by dehydration of the oximino compound and the cyano compound then converted to carboxy or carbalkoxy by known hydrolysis or alcoholysis reaction. The condensation with the oxime is usually carried out in a reaction solvent, preferably but not essentially, in the presence of base catalyst, such as alkali metal salts of organic carboxylic acids such as salts of acetic acid, e.g., sodium acetate. The use of temperatures higher than room temperature merely shortens the requisite reaction time. Temperatures from 0° C. up to 150° C. can be used.

Compounds in which m=1, i.e., the N-oxides, can be formed by reaction of corresponding compounds in which m=0 with peroxide or equivalent peracids. Thus reaction is effected with hydrogen peroxide, perbenzoic acid, peracetic acid, and other peroxides commonly used for this purpose. Generally, the N-oxide formation is carried out at room temperature or lower, to as low as 0° C., for example. For convenience, the starting compound may be dissolved in a suitable reaction solvent. Although only equivalent amounts of peroxide are required, usually excess is used to assure complete reaction.

Solvents employed in the present preparative processes may be any of those commonly used in organic preparations such as dioxane, tetrahydrofuran, dimethyl acetamide, dimethyl formamide and similar solvents. Solvents are not always necessary, however, since the condensation of compounds of formula III with those of formula IV can be carried out without solvent by mere mixing of the reactants, preferably with use of reaction temperatures above room temperature, up to above 150° C. and preferably from about 50° to about 125° C.

The invention will be more fully illustrated in the examples which follow. These examples are given by way of illustration and are not considered as limiting.

EXAMPLE 1

A. 5-Chloro-7-nitro-8-hydroxyquinoline

To a solution of 5-chloro-8-hydroxyquinoline (90.0 g, 0.5 mol) in sulfuric acid (500 ml) at 0° C. was added 90% nitric acid (0.6 mol) at such a rate that the temperature did not exceed 2° C. The clear solution was stirred for one hour at 0° C., and then allowed to slowly warm to room temperature. The mixture was poured into ice (2 liter) and stirred overnight. The yellow precipitate was filtered, washed with water and dried. The yellow cake was crystallized from methylethylketone giving 85.0 g (76% yield) of solid. M.P. 192°–194° C.

B. 5-Chloro-7-amino-8-hydroxyquinoline

To a suspension of 5-chloro-7-nitro-8-hydroxyquinoline (85.0 g, 0.38 mol) in a 1:1 mixture of methanol and water (2.5 liter) was added sodium dithionite (340 g, 2.0 mol). The reaction which is slightly exothermic was stirred overnight under nitrogen. The yellow solid was filtered, washed with water and crystallized from ethanol giving 52 g (70% yield) of solid. M.P. 162°–164° C.

C. 2-Carbomethoxy-5-chloro-1,3-oxazolo-[4,5-h]quinoline

A mixture of 5-chloro-7-amino-8-hydroxyquinoline (6 g, 30.8 mol) and methyl trimethoxyacetate (16.3 g, 123.2 mol) was heated at 100° C. overnight. The reaction was cooled in an ice bath and filtered. The precipitate was dissolved in acetone (250 ml). The resulting solution was treated with charcoal at reflux, filtered through a pad of silica gel and celite and partially concentrated. Crystals formed which were filtered and dried giving 4.1 g (51% yield) of solid. M.P. 217°–218° C.

EXAMPLE 2

A. 2-Formyloximino-5-chloro-1,3-oxazolo-[4,5h]quinoline

A solution of chloral hydrate (1.7 g, 10 mmol) in water (10 ml) containing an equivalent amount of hydroxylamino to form the oxime was heated at 60° C. for three hours. Then a solution of 5-chloro-7-amino-8-hydroxyquinoline (0.9 g, 4.6 mmol) in DMF (10 ml) was added. To this mixture was added sodium acetate (3.2 g, 40 mmol) portionwise over a two hour period. The reaction was heated at 60° C. for an additional hour. The solvent was removed in vacuo. The remaining material was triturated with water, filtered and dried. The solid was dissolved in acetone, treated with charcoal and filtered through a pad of celite and silica gel. The solvent was removed giving the desired product. M.P. 220° C.-dec.

B. 2-Cyano-5chloro-1,3-oxazolo-[4,5-h]quinoline

A suspension of 2-formyloximino-5-chloro-1,3-oxazolo [4,5-h]quinoline (0.7 g, 2.8 mmol) in toluene (300 ml) was treated with thionyl chloride (0.3 ml) and refluxed for one hour. The reaction was filtered and concentrated. The remaining material was dissolved in acetone and filtered through a pad of silica gel and celite. The solvent was removed giving the desired product. M.P. 214°–215° C.

C. 2-Carbomethoxy-5-chloro-1,3-oxazolo-[4,5-h]quinoline

A solution of 5 g of 2-cyano-5-chloro-1,3-oxazolo-[4,5-h]quinoline in 100 ml of methanol was cooled to 0° C. and dry HCl was bubbled through the solution for 1 hour. The solution was then maintained at 0° C. for 24 hours, then allowed to warm up to room temperature. The solvent was removed in vacuo and the residue was dissolved in acetone and filtered through a pad of silica gel and celite. The solvent was removed to give the desired product. M.P. 214°–215° C.

EXAMPLES 3–4

In like manner as above using 7-amino-5-chloro-8-hydroxyquinoline and the appropriate ortho esters or imidates, the following compounds were prepared:
3. 5-chloro-1,3-oxazolo-[4,5-h]quinoline 2-acetic acid, ethyl ester. M.P. 118°–121° C.
4. 2-carboethoxy-5-chloro-1,3-oxazolo-[4,5-h]quinoline. M.P. 150°–152° C.

EXAMPLES 5–13

The following compounds can be made using the above procedure and the appropriate aminoquinolines and imidates or ortho esters:
5. 8-methyl-2-carbomethoxy-1,3-oxazolo-[4,5-h]quinoline.
6. 5-(N,N-dimethylamino)-2-carbomethoxy-1,3-oxazolo-[4,5-h]quinoline.
7. 2-carboethoxy-1,3-oxazolo-[4,5-h]quinoline.
8. 8-trifluoromethyl-2-carbomethoxy-1,3-oxazolo-[4,5-h]quinoline.
9. 5-cyano-1,3-oxazolo-[4,5-h]quinoline-2-propanoic acid, methyl ester.
10. 5-bromo-2-(5-tetrazolyl)-1,3-oxazolo-[4,5-h]quinoline.
11. 5-methyl-2-carbopentoxy-1,3-oxazolo-[4,5-h]quinoline.
12. 2-carboxy-5-trifluoromethyl-1,3-oxazolo-[4,5-h]quinoline ethoxyethyl ester.
13. 2-carboxy-5-nitro-1,3-oxazolo-[4,5-h]quinoline diethylaminoethyl ester.

EXAMPLE 14

5-chloro-1,3-oxazolo-[4,5-h]quinoline-2-carboxylate, sodium salt

A suspension of 2-carboethoxy-5-chloro-1,3-oxazolo[4,5-h]quinoline (1.5 g) in water (100 ml) was treated with 16.3 ml of 1N NaOH. After 10 minutes, the aqueous phase was extracted with chloroform. The aqueous phase was then treated with saturated ammonium chloride causing a white precipitate to form. The filtrate was concentrated in vacuo giving 0.9 g of solid, M.P. 212°–216° C. which was suspended in water (50 ml), treated with one equivalent of sodium hydroxide, and lyophilized to give 0.9 g of product. M.P. 200° C.-dec.

EXAMPLE 15

In like manner as above using the appropriate base, the following salt was prepared:
5-chloro-1,3-oxazolo-[4,5-h]quinoline-2-carboxylate, tris(hydroxymethyl)amino methane salt. M.P. 90° C.-dec.

EXAMPLE 16

2-(5-tetrazolyl)-5-chloro-1,3-oxazolo-[4,5-h]quinoline

A mixture of 5 g of 2-cyano-5-chloro-1,3-oxazolo-[4,5-h]quinoline and 1.0 g of sodium azide and 2 g of ammonium chloride in 100 ml of DMF are heated for 3 hours at 120° C. The reaction mixture is poured into water acidified with dilute HCl, and the product is filtered and recrystallized.

EXAMPLE 17

Other compounds within the current invention which can be prepared include the following in which $R_1$, $R_2$ and X can be as disclosed above.
(A) Oxazolo-[5,4-h]quinolines as, for example, 2-carbomethoxy-1,3-oxazolo-[5,4-h]quinoline
(B) Imidazo-[4,5-h]quinolines as, for example, 2-carbomethoxy-1,3-imidazo-[4,5-h]quinoline
(C) Thiazolo-[4,5-h]quinolines as, for example, 2-carbomethoxy-1,3-thiazolo-[4,5-h]quinoline, and 2-carbomethoxy-1,3-thiazolo-[4,5-h]quinoline-N-oxide
(D) Thiazolo-[5,4-h]quinolines as, for example, 2-carbomethoxy-1,3-thiazolo-[5,4-h]quinoline
(E) Oxazolo-[4,5-h]quinolines as, for example, 2-carbomethoxy-5-chloro-1,3-oxazolo-[4,5-h]quinoline-N-oxide; and
2-formyloximino-5-chloro-1,3-oxazolo-[4,5-h]quinoline

EXAMPLE 18

2-Oxo-3H-oxazolo[4,5-h]quinoline

A suspension of 7-amino-8-hydroxyquinoline (3.2 g, 20.0 mmol) in methylene chloride (50 ml) was treated with 25 ml of 1.6M phosgene gas in methylene chloride. Triethylamine (12 ml) was slowly added and the reaction was stirred overnight. The reaction mixture was partially concentrated and water was added. After treating the resulting mixture with aqueous ammonium hydroxide a precipitate formed which was filtered and dried giving 3.4 g (91% yield) of solid. M.P. >300° C.

EXAMPLE 19

In a similar manner to Example 18, starting with 5-chloro-7-amino-8-hydroxyquinoline, the following compound was prepared:

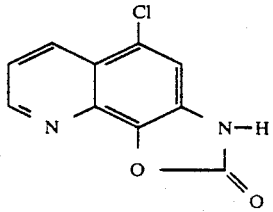

EXAMPLE 20

3-Acetyl-2-oxo-3H-oxazolo[4,5-h]quinoline

A suspension of 2-oxo-3H-oxazolo[4,5-h]quinoline (1.86 g, 10.0 mmol), acetic anhydride (50 ml) and sulfuric acid (0.5 ml) was refluxed overnight. The reaction was filtered and the filtrate concentrated. Methylene chloride was added and the resulting solution was washed (3×) with water, brine; dried over $MgSO_4$ and concentrated to a solid. The solid was crystallized from ethanol to give 1.82 g (80% yield) of product. M.P. 192°–193° C.

EXAMPLES 21-24

In like manner as in Example 20, using appropriate starting materials and reagents, the following compounds were prepared:

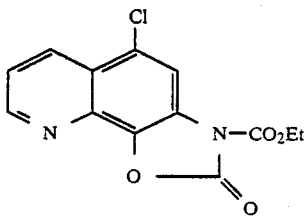
21.

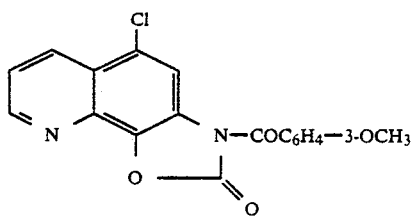
22.

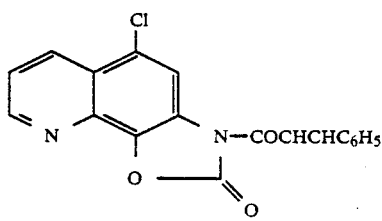
23.

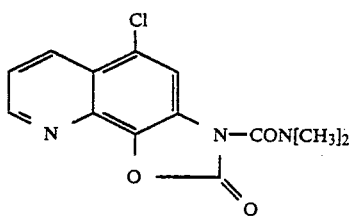
24.

EXAMPLE 25

5-Chloro-3-methyl-2-oxo-3H-oxazolo[4,5-h]quinoline

To a solution of 5-Chloro-7-amino-8-hydroxyquinoline (3.0 g, 13.6 mmol), degreased sodium hydride (1.0 g, 50% in oil) and DMF at 60° C. was added methyl iodide. The reaction was stirred for 1 hour. Water was added and the mixture was extracted with chloroform (3×). The organic extracts were combined and concentrated. The remaining solid was crystallized from ethanol to give 1.4 g (45% yield) of product. M.P. 219°–221° C.

The compounds of this invention are useful as antiallergy agents as determined by testing in the following procedures recognized to be cognent in vitro and in vivo models of human allergic disease.

A. The PCA Test

The compounds of this invention have potent activity in inhibiting the formation of a wheel when screened according to the Rat Passive Cutaneous Anaphylaxis (PCA) Screen as described by I. Mota, Life Sciences, 7, 465 (1963) and Z. Ovary, et al. Proceedings of Society of Experimental Biology and Medicine, 81, 584 (1952).

B. The RMC Test

In addition, the compounds of this invention have potent activity as inhibitors of histamine release from passively sensitized Rat Mast Cells according to the porcedure described by E. Kusner, et al., Journal of Pharmacology and Experimental Therapeutics, 184, 41 (1973).

When screened according to the above procedures, the compounds of this invention showed potent antiallergic activity and, as such, are useful in the treatment of conditions such as asthma. In the RMC test, $I_{50}$ values of from 1 to 100 μm were found; in the PCA test, $ED_{50}$ values of from 1 to 50 mg/kg were found. By way of illustration, the compound of example 1C had an $I_{50}$ value of 0.3 μm in the RMC test and $E_{50}$ value of 0.5 mg/kg and 1.0 mg/kg when administered by the intraperitoneal route and oral routes respectively in PCA test. The compound of example 4 had an $I_{50}$ value of 0.1 μm in the RMC test and 59% inhibition of wheal formation at 10 mg/kg in the PCA test on intraperitoneal administration. The compound of example 14 had an $I_{50}$ of 0.1 μm in the RMC test and 51% inhibition of wheal formation at 10 mg/kg in the PCA test on intraperitoneal administration.

Additional illustrative results are shown in Table I, for the compounds of Examples 18 through 25.

TABLE I

| Com- pounds | RMC % inh. (μm) | RMC $IC_{50}$ μM | PCA % inh. IP (mg/kg) | PCA PO (mg/kg) | PCA $ED_{50}$ IP mg/kg | PCA $ED_{50}$ PO mg/kg |
|---|---|---|---|---|---|---|
| Example 18 | <30(50)b | | | | 10 | 4 |
| Example 19 | | | | 0(25) | | |
| Example 20 | 18(50) | | | 14(125) | | |
| Example 21 | 87(50) | | | 15(100) | | |
| Example 22 | c | | | 43(100) | | |
| Example 23 | 16(50) | | 34(125) | | | |
| Example 24 | 18(50) | | | 0(25) | | |
| Example 25 | 0(50) | | | 51(125) | | |

What is claimed is:
1. A quinoline compound of the formula:

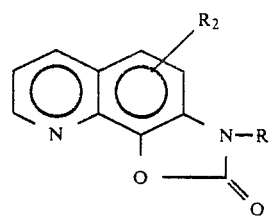

and salts thereof, wherein
 R is hydrogen, acetyl, methoxybenzoyl, carboethoxy, (2-phenyl)propionyl, dimethylcarbamoyl or methyl, and
 $R_2$ is hydrogen, lower alkyl, halo, trifluoromethyl, amino, lower alkyl amino cyano, aryl, aryl/lower alkylene, lower alkynyl, lower alkenyl, nitro, lower alkyl sulfinyl, lower alkyl sulfonyl, lower alkoxycarbonyl, carboxyl, lower alkoxy, lower alkanoyl, or lower alkenoyl.

2. A pharmaceutical composition for the treatment of allergic conditions in a mammal which comprises as an active ingredient a therapeutically effective amount of a compound or its salt according to claim 1 in admixture with an inert pharmaceutically acceptable carrier.

3. A method of treating allergic conditions in a mammal which method comprises administering to said mammal requiring treatment a therapeutically effective amount of the composition of claim 2.

* * * * *